United States Patent
Rissmann et al.

(10) Patent No.: US 6,865,417 B2
(45) Date of Patent: Mar. 8, 2005

(54) H-BRIDGE WITH SENSING CIRCUIT

(75) Inventors: William J. Rissmann, Coto de Caza, CA (US); Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 354 days.

(21) Appl. No.: 10/011,946

(22) Filed: Nov. 5, 2001

(65) Prior Publication Data

US 2003/0088279 A1 May 8, 2003

(51) Int. Cl.$^7$ ................................................ A61N 1/39
(52) U.S. Cl. ................................................ 607/5
(58) Field of Search .................................... 607/4–5, 8

(56) References Cited

U.S. PATENT DOCUMENTS

| | | | |
|---|---|---|---|
| 3,653,387 A | * 4/1972 | Ceier ........................... | 600/525 |
| 3,710,374 A | 1/1973 | Kelly ........................... | 341/167 |
| 4,191,942 A | 3/1980 | Long ........................... | 341/124 |
| 4,223,678 A | 9/1980 | Langer et al. ................. | 607/5 |
| 4,402,322 A | 9/1983 | Duggan ........................ | 607/9 |
| 4,407,288 A | 10/1983 | Langer et al. ................. | 607/4 |
| 4,602,637 A | 7/1986 | Elmqvist et al. .............. | 607/36 |
| 4,800,883 A | 1/1989 | Winstrom ...................... | 607/7 |
| 4,830,005 A | 5/1989 | Woskow ........................ | 607/27 |
| 5,109,842 A | 5/1992 | Adinolfi ....................... | 607/2 |
| 5,129,392 A | 7/1992 | Bardy et al. .................. | 607/2 |
| 5,144,946 A | 9/1992 | Weinberg et al. .............. | 607/2 |
| 5,184,616 A | 2/1993 | Weiss .......................... | 607/4 |
| 5,331,966 A | 7/1994 | Bennett et al. ............... | 600/508 |
| 5,376,103 A | 12/1994 | Anderson et al. .............. | 607/5 |
| 5,376,104 A | 12/1994 | Sakai et al. .................. | 607/5 |
| 5,411,547 A | 5/1995 | Causey, III .................. | 607/129 |
| 5,413,591 A | 5/1995 | Knoll .......................... | 607/6 |
| 5,507,781 A | 4/1996 | Kroll et al. .................. | 607/7 |
| 5,531,765 A | 7/1996 | Pless .......................... | 607/5 |
| 5,601,607 A | 2/1997 | Adams ......................... | 607/5 |
| 5,658,317 A | 8/1997 | Haefner et al. ................ | 607/5 |
| 5,674,260 A | 10/1997 | Weinberg ..................... | 607/36 |
| 5,690,683 A | 11/1997 | Haefner et al. ................ | 607/4 |
| 5,697,953 A | 12/1997 | Kroll et al. .................. | 607/5 |
| 5,713,926 A | 2/1998 | Hauser et al. ................. | 607/5 |
| 5,718,242 A | 2/1998 | McClure et al. ............... | 600/515 |

(List continued on next page.)

FOREIGN PATENT DOCUMENTS

| | | | | |
|---|---|---|---|---|
| EP | 0 316 616 A2 | 5/1989 | ............ | H03M/1/54 |
| EP | 0 347 353 A1 | 12/1989 | ............ | A61N/1/39 |
| EP | 0 518 599 B1 | 6/1992 | ............ | A61N/1/39 |
| EP | 0 518 599 A2 | 6/1992 | ............ | A61N/1/39 |
| EP | 0 536 873 B1 | 7/1992 | ............ | A61N/1/39 |

(List continued on next page.)

OTHER PUBLICATIONS

Olson, Walter H. et al. "Onset and Stability for Ventricular Tachyarrhythmia Detection in an Implantable Pacer–Cardioverter–Defibrillator," *IEEE* (1987) pp. 167–170.

(List continued on next page.)

*Primary Examiner*—Carl Layno
(74) *Attorney, Agent, or Firm*—Crompton, Seager & Tufte, LLC

(57) ABSTRACT

In a cardioverter/defibrillator system, an electrical circuit includes an energy storage device, an output circuit for controlling delivery of pulse therapy from the energy storage device to a patient, and a sensing circuit coupled across the patient to sense the patient's heart signal. The output circuit may be in the form of an H-bridge switching circuit wherein a pair of switches of the output circuit is simultaneously turned on to discharge residual voltage across the patient that remains after delivery of pulse therapy. Thus, interference with sensing of the patient's heart signal is avoided.

49 Claims, 2 Drawing Sheets

U.S. PATENT DOCUMENTS

| | | | |
|---|---|---|---|
| 5,766,226 A | 6/1998 | Pedersen | 607/5 |
| 5,836,976 A | 11/1998 | Min et al. | 607/6 |
| 5,919,211 A | 7/1999 | Adams | 607/5 |
| 5,935,154 A | 8/1999 | Westlund | 607/36 |
| 5,941,904 A | 8/1999 | Johnston et al. | 607/19 |
| 6,014,586 A | 1/2000 | Weinberg et al. | 607/36 |
| 6,026,325 A | 2/2000 | Weinberg et al. | 607/36 |
| 6,058,328 A | 5/2000 | Levine et al. | 607/14 |
| 6,096,063 A | 8/2000 | Lopin et al. | 607/8 |
| 6,128,531 A | 10/2000 | Campbell-Smith | 607/7 |
| 6,144,866 A | 11/2000 | Miesel et al. | 600/333 |
| 6,169,921 B1 * | 1/2001 | KenKnight et al. | 607/4 |
| 6,185,450 B1 | 2/2001 | Seguine et al. | 600/509 |
| 6,208,895 B1 * | 3/2001 | Sullivan et al. | 607/4 |
| 6,241,751 B1 | 6/2001 | Morgan et al. | 607/8 |
| 6,411,844 B1 | 6/2002 | Kroll et al. | 607/5 |
| 2001/0027330 A1 | 10/2001 | Sullivan et al. | 607/4 |

FOREIGN PATENT DOCUMENTS

| | | | |
|---|---|---|---|
| EP | 0 641 573 A2 | 8/1994 | A61N/1/39 |
| EP | 0 641 573 A3 | 8/1994 | A61N/1/39 |
| EP | 0 917 887 A1 | 10/1998 | A61N/1/368 |
| EP | 0 923 130 A1 | 7/2001 | H01L/23/538 |
| WO | WO 93/19809 A1 | 10/1993 | A61N/1/39 |
| WO | WO 98/25349 A1 | 6/1998 | H03M/1/56 |
| WO | WO 99/03534 A1 | 1/1999 | A61N/1/39 |
| WO | WO 99/37362 A1 | 7/1999 | A61N/1/38 |
| WO | WO 01/56166 A2 | 8/2001 | H03M/1/54 |
| WO | WO 02/22208 A2 | 3/2002 | A61N/1/39 |
| WO | WO 02/22208 A3 | 3/2002 | A61N/1/39 |
| WO | WO 02/24275 A3 | 3/2002 | A61N/1/39 |
| WO | WO 02/24275 A2 | 3/2002 | A61N/1/39 |
| WO | WO 02/068046 A1 | 9/2002 | A61N/1/37 |
| WO | WO 03/018121 A2 | 3/2003 | A61N/1/375 |

OTHER PUBLICATIONS

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95–123.

Schuder, John C. et al., "Experimental Ventricular Defibrillation with an Automatic and Completely Implanted System," *Trans. Amer. Soc. Artif. Int. Organs*, vol. XVI (1970) pp. 207–212.

Shuder, John C. et al., "Transthoracic Ventricular Defibrillation in the Dog with Truncated and Untruncated Exponential Stimuli," *IEEE Transactions on Bio–Medical Engineering*, vol. BME 18, No. 6, Nov. 1971, pp. 410–415.

Tietze, U. et al., "Halbleiter–Schaltungstechnik," *Springer–Verlag*, Berlin, Germany (1991) pp. 784–786.

Walters, R.A. et al., "Analog to Digital Conversion Techniques in Implantable Devices," *Annual International Conference of the IEEE Engineering in Medicine and Biology Society*, vol. 13, No. 4 (1991) pp. 1674–1676.

* cited by examiner

H-BRIDGE WITH SENSING CIRCUIT

RELATED APPLICATIONS

The present application may find use in systems such as are disclosed in the U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, pending, and U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, pending, of which both applications are assigned to the assignee of the present application, and the disclosures of both applications are hereby incorporated by reference.

Applications related to the foregoing applications include a U.S. patent application entitled "DUCKBILL-SHAPED IMPLANTABLE CARDIOVERTER-DEFIBRILLATOR AND METHOD OF USE," U.S. patent application entitled "CERAMICS AND/OR OTHER MATERIAL INSULATED SHELL FOR ACTIVE AND NON-ACTIVE S-ICD CAN," U.S. patent application entitled "SUBCUTANEOUS ELECTRODE FOR TRANSTHORACIC CONDUCTION WITH IMPROVED INSTALLATION CHARACTERISTICS," U.S. patent application entitled "SUBCUTANEOUS ELECTRODE WITH IMPROVED CONTACT SHAPE FOR TRANSTHORACIC CONDUCTION," U.S. patent application entitled "SUBCUTANEOUS ELECTRODE FOR TRANSTHORACIC CONDUCTION WITH HIGHLY MANEUVERABLE INSERTION TOOL," U.S. patent application entitled "SUBCUTANEOUS ELECTRODE FOR TRANSTHORACIC CONDUCTION WITH LOW-PROFILE INSTALLATION APPENDAGE AND METHOD OF DOING SAME," U.S. patent application entitled "SUBCUTANEOUS ELECTRODE FOR TRANSTHORACIC CONDUCTION WITH INSERTION TOOL," U.S. patent application entitled "METHOD OF INSERTION AND IMPLANTATION FOR IMPLANTABLE CARDIOVERTER-DEFIBRILLATOR CANISTERS," U.S. patent application entitled "CANISTER DESIGNS FOR IMPLANTABLE CARDIOVERTER-DEFIBRILLATORS," U.S. patent application entitled "RADIAN CURVED IMPLANTABLE CARDIOVERTER-DEFIBRILLATOR CANISTER," U.S. patent application entitled "CARDIOVERTER-DEFIBRILLATOR HAVING A FOCUSED SHOCKING AREA AND ORIENTATION THEREOF," U.S. patent application entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application entitled "BIPHASIC WAVEFORM FOR ANTI-TACHYCARDIA PACING FOR A SUBCUTANEOUS IMPLANTABLE CARDIOVERTER-DEFIBRILLATOR," the disclosures of which applications are hereby incorporated by reference.

FIELD OF THE INVENTION

The present invention relates generally to defibrillation/cardioversion systems, and more particularly, to a defibrillation/cardioversion system having an H-bridge with a sensing circuit used in pacing and shocking the heart.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705, 4,693,253, 4,944,300, 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Typically, ICDs generate an electrical shock by charging a capacitance system to a high voltage from a low voltage power source and oscillator circuit. Then, the power source is switched out of the circuit and the electrical charge stored in the capacitance system is discharged through electrodes implanted in a patient.

Typical discharge waveforms used with ICDs include monophasic, biphasic or multiphasic waveforms delivered as capacitance discharges. A monophasic waveform is comprised of a single monotonically decaying electrical pulse typically truncated before complete discharging of the capacitance system.

Biphasic waveforms are comprised of a decaying electrical pulse having a pair of decaying electrical phases of opposite polarity. To generate a biphasic pulse, an H-bridge switch circuit is used, which is connected to the implanted electrodes. The H-bridge switches the polarity of the two phases. In generating the biphasic pulse, a first phase is discharged from the capacitance system, similar to a monophasic pulse. When the first pulse is truncated, the H-bridge switch circuit immediately reverses the discharge polarity of the capacitance system as seen by the electrodes to generate the second phase of the biphasic waveform being of opposite polarity.

An H-bridge may be used in defibrillators that deliver high voltage electrical pulses, or shock, and also lower energy pacing pulses to a patient. After a shock or pacing energy is delivered to a patient, normally there is residual voltage on implanted electrodes on the patient such that the sensing ability of those electrodes is reduced, thus hindering the observation of a heart signal through an electrocardiogram.

What is needed, therefore, is a defibrillator with an H-bridge switch circuit such that residual voltage is dissipated from electrodes after a shock or pacing energy is delivered to a patient so that sensing activity is not affected.

SUMMARY OF THE INVENTION

An electrical circuit for a cardioverter-defibrillation system includes an energy storage device such as a capacitor, an output circuit for controlling delivery of defibrillation pulses from the energy storage device to a patient, and a sensing circuit coupled across the patient to sense the patient's heart signal. The output circuit may be in the form of an H-bridge switching circuit wherein a pair of switches of the output circuit is simultaneously turned on to discharge residual voltage across the patient that remains after delivery of defibrillation pulses. Thus, interference with sensing of the patient's heart signal is avoided.

BRIEF DESCRIPTION OF THE DRAWINGS

For a better understanding of the invention, reference is now made to the drawings where like numerals represent similar objects throughout the figures where.

DETAILED DESCRIPTION OF THE INVENTION

Figure 1:
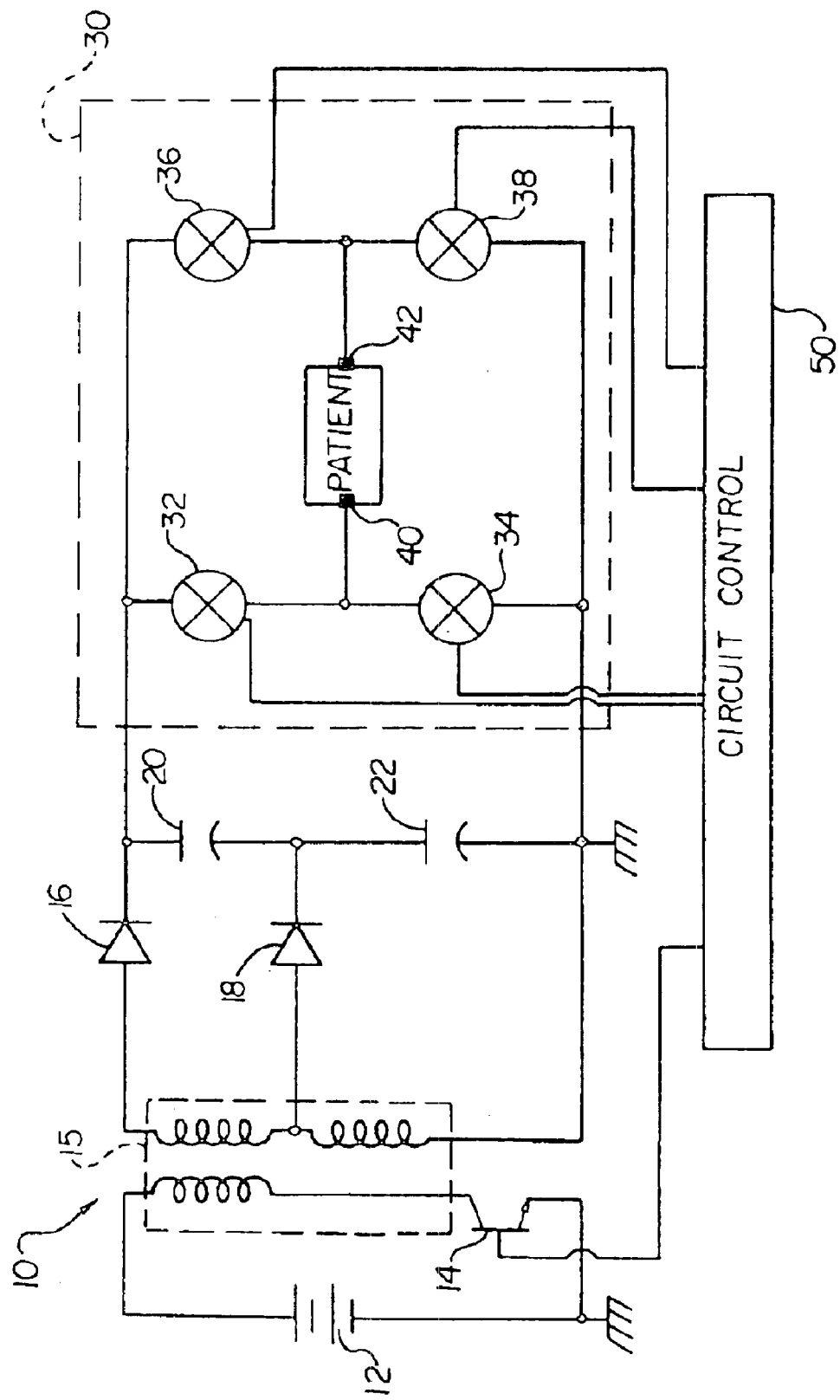
FIG. 1 is a schematic diagram of a typical ICD circuit including an H-bridge output circuit.

Referring first to FIG. 1, a schematic diagram of a typical ICD circuit including an H-bridge output circuit is illustrated. Circuit 10 includes a battery power source 12; a double secondary fly back transformer 15; a transistor switch 14; rectifying diodes 16, 18; high voltage storage capacitors 20, 22; circuit control 50; an output circuit 30 having four legs arranged in the form of an "H" (an "H-bridge 30"), each leg of the H-bridge 30 having switches 32, 34, 36, and 38, respectively; and cardiac electrodes 40, 42.

The H-bridge 30 is connected to cardiac electrodes 40, 42, and is used to generate a biphasic pulse. The H-bridge 30 switches the polarity of the two phases. A first phase is discharged from the high voltage storage capacitors 20, 22 by activating switches 32 and 38. Then the first phase is truncated, and the H-bridge 30 activates switches 36 and 34, and reverses the discharge polarity of the high voltage storage capacitors 20, 22 from the point of view of the cardiac electrodes 40, 42, to generate the second phase of the waveform with opposite polarity.

Figure 2:
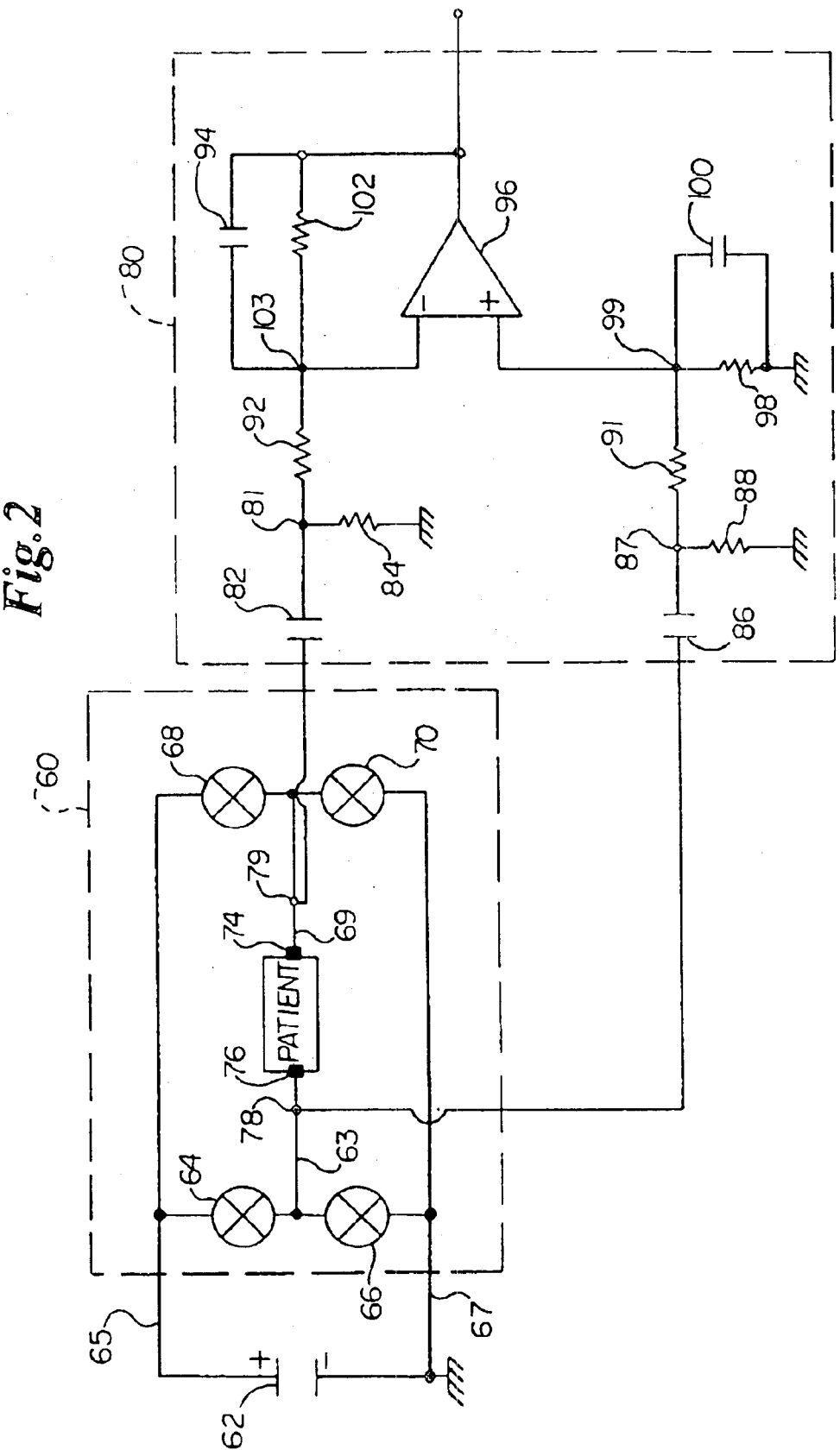
FIG. 2 is a schematic diagram of an H-bridge with sensing circuitry according to an embodiment of the present invention.

Referring now to FIG. 2, a schematic diagram of an H-bridge with sensing circuitry according to an embodiment of the present invention is illustrated. An energy storage capacitor 62 is connected to an H-bridge 60. A sensing circuit 80 is connected across a patient at nodes 78 and 79 of the H-bridge 60.

It should be appreciated that a variety of H-bridge output circuits such as the one described with respect to FIG. 1 may be used within the scope of the present invention. Furthermore, it should be noted that additional semiconductor switches may be incorporated in each leg of the H-bridge to reduce the voltage that must be switched by each switch.

Although FIG. 2 shows a single energy storage capacitor 62, it is well-understood in the art that a bank of capacitors may be used, or any other energy storage device. The energy storage capacitor 62 can be charged to a range of voltage levels, with the selected level depending on the patient and other parameters. The typical maximum voltage necessary for ICDs using most biphasic waveforms is approximately 750 Volts with an associated maximum energy of approximately 41 Joules. For subcutaneous ICDs, the maximum voltages used may be in the range of about 50 to about 3150 Volts and are associated with energies of about 0.5 to about 350 Joules. The energy storage capacitor 62 may be controlled to deliver either defibrillation or pacing energy, and could range from about 25 to about 200 micro farads for a subcutaneous ICD.

After charging to a desired level, the energy stored in capacitor 62 may be delivered to the patient in the form of a defibrillation pulse or pacing energy. H-bridge 60 is provided as an output circuit to allow the controlled transfer of energy from the energy storage capacitor 62 to the patient.

Each leg of the H-bridge 60 contains a solid-state switch 64, 66, 68, and 70. Switches 64, 66, 68, and 70 may be silicon controlled rectifiers (SCRs), insulated gate bipolar transistors (IGBTs), or MOSFETs. H-bridge 60 further includes electrodes 74 and 76 coupled to a patient.

Switches 64 and 68 are coupled to the positive lead of the energy storage capacitor 62 via bridge line 65. It should be noted that a protective circuit (not shown) with inductive and resistive properties may be added, for example, at bridge line 65 between the positive lead of the capacitor 62 and the switch 64 to limit current and voltage changes from the storage capacitor 62 during a defibrillation pulse. Switches 66 and 70 are coupled to the negative lead of the energy storage capacitor 62 via a bridge line 67. The patient is connected to the left side of the H-bridge by a line 63 and to the right side of the H-bridge by a line 69. Line 63 is connected to electrode 76 and line 69 is connected to electrode 74.

By selectively switching on pairs of switches in the H-bridge, a biphasic defibrillation pulse may be applied to the patient. Embodiments of the present invention may also use monophasic or multiphasic defibrillation pulses. The switches in the H-bridge are biased with a voltage that allows them to remain turned-on even when conducting low current.

When the energy storage capacitor 62 is charged to a selected energy level, the switches 64 and 70 may be turned on to connect the energy storage capacitor 62 with lines 63 and 69 for the application of a first phase of a defibrillation pulse to the patient. The stored energy travels from the positive terminal of the energy storage capacitor 62 on line 65, through switch 64 and line 63, across the patient, and back through line 69 and switch 70 to the negative terminal of the capacitor. The first phase of the biphasic pulse is therefore a positive pulse. Before the energy storage capacitor 62 is completely discharged, the switch 70 is biased off to prepare for the application of the second phase of the biphasic pulse. Once the switch 70 is biased off, switch 64 will also become non-conductive because the voltage falls to zero.

After the end of the first phase of the biphasic defibrillation pulse, switches 68 and 66 are switched on to start the second phase of the biphasic pulse. Switches 68 and 66 provide a path to apply a negative defibrillation pulse to the patient. The energy travels from the positive terminal of the energy storage capacitor 62 on line 65, through switch 68 and line 69, across the patient, and back through line 63 and switch 66 to the negative terminal of the energy storage capacitor. The polarity of the second phase of the defibrillation pulse is therefore opposite in polarity to the first phase of the biphasic pulse. The end of the second phase of the biphasic pulse may be truncated by switching on switch 64 to provide a shorted path for the remainder of the capacitor energy through switches 64 and 66. Digital logic (not shown) may be used to control the sequencing of the switches 64, 66, 68, and 70 such that the polarity can be inverted so that the first phase is negative instead of positive. The digital logic generally controls the timing, the duration of each phase and the inter phase delay.

Sensing circuit 80 is connected to H-bridge 60 across the patient at nodes 78 and 79. Sensing circuit 80 includes a sense amplifier 96 that senses differentially and is capacitively coupled across the patient. The sense amplifier 96 has a negative lead connected to node 79 in the H-bridge 60 through a capacitor 82. A resistor 84 is connected to capacitor 82 between ground and node 81 in a high-pass filter of approximately 0.5–20 Hz. Resistor 84 may range in value between approximately 10 KΩ and 500 KΩ. A resistor 92 is connected between node 81 and node 103. A capacitor 94 and a resistor 102 are connected in parallel at node 103 as a low pass filter of approximately 30–150 Hz. It should be appreciated that there could be multiple low pass filters as well as multiple high pass filters connected to the negative lead of the sense amplifier 96.

The sense amplifier 96 has a positive lead connected to node 78 via a capacitor 86. A resistor 88 is connected to capacitor 86 between ground and node 87 in a high-pass filter of approximately 0.5–20 Hz. A resistor 91 is connected between node 87 and node 99. A capacitor 100 and a resistor 98 are connected in parallel at node 99 as a low pass filter of approximately 30–150 Hz. It should be appreciated that there could be multiple low pass filters as well as multiple high pass filters connected to the positive lead of the sense amplifier 96. Furthermore, an embodiment of the sensing circuit may comprise digital logic for overall control of the sensing circuit.

The sensing circuit 80 allows constant observation of heart signals as an electrocardiogram. When it is time to deliver therapy, a shock or pacing energy is delivered as required. Switches 64, 70, 68, and 66 of the H-bridge 60 are sequenced to deliver monophasic, biphasic, or multiphasic pulses. During shock or even during pacing, as soon as the therapy pulse is completed, there may be a residual voltage that remains on electrodes 74 and 76 as they are not simply resistors. Capacitances may be involved in the patient such that after a pacing pulse or defibrillation shock there are residual voltages. The residual voltages could, when present, limit the time that it takes for the differential sensing amplifier 96 to recover and allow proper continuing observation of the heart signal and determine whether the heart has returned to a normal rhythm or whether there is still an arrhythmia. Thus, the amplifier needs to recover as soon as possible, for example, in much less than a second, and the voltages have to be within the common mode operating range of the amplifier as soon as possible.

To improve the post-shock or post-pacing recovery time on the amplifiers, switches 66 and 70 of the H-bridge 60 are turned on at the same time to discharge any residual voltage across the patient. By turning on or closing both switches 66 and 70, the voltage across the electrodes 76 and 74 is effectively shorted out and the residual voltage across the patient is removed. If there are any capacitances involved in series or in parallel with the patient, all that energy is dissipated.

After a monophasic, biphasic or multiphasic pacing pulse, or a shock is delivered, switches 6 and 70 are closed sometime after the end of the pulse, for example, after approximately 50 microseconds to 10 milliseconds, for a period of approximately 10 microseconds to up to approximately a second. This will dissipate the residual voltage across the patient, and improve the recovery time of the sense amplifier. Embodiments of the present invention allow the sensing to be done from the H-bridge. To dissipate energy, additional external switches may be used, however, using the switches of the H-bridge itself saves the complexity of using external switches.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined in the language in which the appended claims are expressed.

What is claimed is:

1. An electrical circuit for a cardioverter-defibrillation system comprising:
   an energy storage device;
   an output circuit coupled to the energy storage device, wherein the output circuit comprises a plurality of switching means for controlling delivery of defibrillation pulses from the energy storage device to a patient; and
   a sensing circuit coupled across the patient to sense a patient's heart signal, wherein at least two of the switching means of the output circuit are simultaneously turned on to discharge residual voltage across the patient, thus avoiding interference with sensing of the patient's heart signal.

2. The electrical circuit of claim 1, wherein the cardioverter/defibrillation system further comprises an implantable cardioverter defibrillator.

3. The electrical circuit of claim 2, wherein the cardioverter/defibrillation system further comprises a subcutaneous implantable cardioverter defibrillator.

4. The electrical circuit of claim 1, wherein the output circuit further comprises an H-bridge output circuit.

5. The electrical circuit of claim 1, wherein the sensing circuit further comprises a differential amplifier.

6. The electrical circuit of claim 1, wherein the switching means further comprises at least one SCR.

7. The electrical circuit of claim 1, wherein the switching means further comprises at least one IGBT.

8. The electrical circuit of claim 1, wherein the switching means further comprises at least one MOSFET.

9. The electrical circuit of claim 1, wherein the sensing circuit further comprises digital logic for control.

10. The electrical circuit of claim 1, wherein the output circuit is sequenced to deliver a biphasic pulse to the patient.

11. The electrical circuit of claim 1, wherein the output circuit is sequenced to deliver a monophasic pulse to the patient.

12. The electrical circuit of claim 1, wherein the output circuit is sequenced to deliver a multiphasic pulse to the patient.

13. The electrical circuit of claim 1 wherein the sensing circuit further comprises at least one low pass filter.

14. The electrical circuit of claim 1 wherein the sensing circuit further comprises at least one high pass filter.

15. The electrical circuit of claim 14, wherein the high pass filter operates in a frequency range of approximately 1 to 20 Hz.

16. The electrical circuit of claim 13, wherein the low pass filter operates in a frequency range of approximately 30–150 Hz.

17. The electrical circuit of claim 1, wherein the energy storage device further comprises at least one capacitor.

18. An electrical circuit for a cardioverter/defibrillator comprising:
    a storage circuit connected to a power source;
    an output circuit coupled to the storage circuit that controls delivery of defibrillation pulse therapy to a patient; and
    a sensing circuit coupled to the output circuit across the patient such that the sensing circuit immediately recovers after delivery of pulse therapy by removal of residual voltage across the patient;
    wherein the output circuit further comprises an H-bridge.

19. The electrical circuit of claim 18, wherein the cardioverter/defibrillator is implantable in the patient.

20. The electrical circuit of claim 19, wherein the cardioverter/defibrillator further comprises a subcutaneous cardioverter/defibrillator.

21. The electrical circuit of claim 18, wherein the H-bridge further comprises switches.

22. The electrical circuit of claim 21, wherein the switches further comprise at least one SCR.

23. The electrical circuit of claim 21, wherein the switches further comprise at least one IGBT.

24. The electrical circuit of claim 21, wherein the switches further comprise at least one MOSFET.

25. The electrical circuit of claim 18, wherein the storage circuit further comprises at least one capacitor.

26. The electrical circuit of claim 18, wherein the storage circuit is charged to approximately between 0.5 Joules and 350 Joules for internal application to the patient.

27. The electrical circuit of claim 18, wherein the output circuit is sequenced to deliver a biphasic defibrillation pulse to the patient.

28. The electrical circuit of claim 18, wherein the output circuit is sequenced to deliver a monophasic defibrillation pulse to the patient.

29. The electrical circuit of claim 18, wherein the output circuit is sequenced to deliver a multiphasic defibrillation pulse to the patient.

30. The electrical circuit of claim 18, wherein the sensing circuit further comprises a differential amplifier.

31. The electrical circuit of claim 18, wherein the sensing circuit further comprises digital logic for control.

32. An electrical circuit for a cardioverter/defibrillator comprising:
    a storage circuit connected to a power source;
    an output circuit coupled to the storage circuit that controls delivery of defibrillation pulse therapy to a patient; and
    a sensing circuit coupled to the output circuit across the patient such that the sensing circuit immediately recovers after delivery of pulse therapy by removal of residual voltage across the patient;
    wherein the sensing circuit further comprises at least one high-pass filter;

wherein the high-pass filter operates in a frequency range of approximately between 0.5–20 Hz.

33. A method for defibrillating a patient using an implantable cardioverter/defibrillator comprising the steps of:

sensing a heart signal;

sequencing switches of an output circuit to deliver pulse therapy to the patient based on the sensing of the heart signal;

after delivery of the pulse therapy to the patient, turning on at least two switches of the output circuit to discharge residual voltage across the patient that remains after delivery of the pulse therapy.

34. The method of claim 33, wherein the step of sequencing switches of an output circuit to deliver pulse therapy to the patient further comprises delivering a defibrillation shock.

35. The method of claim 33, wherein the step of sequencing switches of an output circuit to deliver pulse therapy to the patient further comprises delivering pacing energy.

36. The method of claim 33, wherein the step of sequencing switches of an output circuit to deliver pulse therapy to the patient further comprises delivering biphasic pulses.

37. The method of claim 33, wherein the step of sequencing switches of an output circuit to deliver pulse therapy to the patient further comprises delivering monophasic pulses.

38. The method of claim 33, wherein the step of sequencing switches of an output circuit to deliver pulse therapy to the patient further comprises delivering multiphasic pulses.

39. The method of claim 33, wherein the step of turning on at least two switches further comprises closing the at least two switches at the same time for a period of approximately 10 microseconds to a second.

40. The method of claim 33 further comprising the step of continuing sensing of the heart signal after delivery of the pulse therapy.

41. A method for sensing a heart signal of a patient and providing pulse therapy to the patient using a subcutaneous implantable cardioverter/defibrillator, the method comprising the steps of:

providing an output circuit having switching means coupled to electrodes proximate to a patient's heart;

providing a sensing circuit coupled across the patient for monitoring the heart signal of the patient;

sequencing the output circuit to deliver therapy pulses to the patient; and when the therapy pulses are completed, turning on a pair of switching means of the output circuit at the same time effectively shorting voltage across the electrodes and discharging residual voltage across the patient, thus avoiding interference with immediate recovery of the sensing circuit and thus allowing proper observation of the heart signal.

42. The method of claim 41, wherein the step of providing an output circuit further comprises providing an H-bridge circuit.

43. The method of claim 41, wherein the step of sequencing the output circuit to deliver therapy pulses to the patient further comprises delivering a defibrillation shock.

44. The method of claim 41, wherein the step of sequencing the output circuit to deliver therapy pulses to the patient further comprises delivering pacing energy.

45. The method of claim 41, wherein the step of sequencing the output circuit to deliver therapy pulses to the patient further comprises delivering biphasic pulses.

46. The method of claim 41, wherein the step of sequencing the output circuit to deliver therapy pulses to the patient further comprises delivering monophasic pulses.

47. The method of claim 41, wherein the step of sequencing the output circuit to deliver therapy pulses to the patient further comprises delivering multiphasic pulses.

48. The method of claim 41, wherein the step of turning on a pair of switching means further comprises closing the pair of switching means at the same time for a period of approximately 10 microseconds to a second.

49. The method of claim 41 further comprising the step of continuing sensing of the heart signal after delivery of the pulse therapy.

* * * * *